US007698752B2

(12) United States Patent
Pennell et al.

(10) Patent No.: US 7,698,752 B2
(45) Date of Patent: Apr. 20, 2010

(54) GOGGLE STRAP

(75) Inventors: Edward Pennell, Dallas, PA (US);
Charles Edward Runco, Olyphant, PA (US)

(73) Assignee: Aramark Cleanroom Services, LLC, Burbank, CA (US)

( * ) Notice: Subject to any disclaimer, the term of this patent is extended or adjusted under 35 U.S.C. 154(b) by 175 days.

(21) Appl. No.: 11/286,048

(22) Filed: Nov. 23, 2005

(65) Prior Publication Data
US 2007/0113326 A1 May 24, 2007

(51) Int. Cl.
*A61F 9/02* (2006.01)
(52) U.S. Cl. .......................................... 2/452; 351/156
(58) Field of Classification Search .................. 2/452, 2/171, DIG. 11; 351/156, 157, 43; 24/3.3; 283/75
See application file for complete search history.

(56) References Cited

U.S. PATENT DOCUMENTS

| 2,264,351 | A | * | 12/1941 | Willson .......................... 2/452 |
| 4,656,671 | A | | 4/1987 | Manges |
| 4,813,459 | A | | 3/1989 | Breidegam |
| 4,910,806 | A | | 3/1990 | Baker et al. |
| 5,046,200 | A | | 9/1991 | Feder |
| 5,617,589 | A | * | 4/1997 | Lacore et al. .................. 2/452 |
| 5,823,409 | A | | 10/1998 | Kennedy |
| 5,826,277 | A | * | 10/1998 | McConville .................... 2/171 |
| 5,890,236 | A | * | 4/1999 | Harges et al. .................. 2/440 |
| 5,958,537 | A | * | 9/1999 | Akhter ...................... 428/40.2 |
| 6,047,410 | A | | 4/2000 | Dondero |
| 6,148,817 | A | | 11/2000 | Bryant et al. |
| 6,269,488 | B1 | | 8/2001 | Jurgensen et al. |
| 6,490,729 | B1 | | 12/2002 | Dondero |
| 6,502,245 | B1 | * | 1/2003 | McBride ........................ 2/181 |
| 6,672,492 | B1 | | 1/2004 | Thompson |
| 6,898,889 | B1 | * | 5/2005 | Toler ........................... 42/111 |
| 6,959,784 | B2 | * | 11/2005 | Diggle et al. .................. 182/9 |
| 7,163,290 | B2 | * | 1/2007 | Paolino ...................... 351/156 |
| 7,195,165 | B2 | * | 3/2007 | Kesler et al. ........... 235/462.01 |
| 7,198,190 | B2 | * | 4/2007 | Juhan et al. .................. 235/380 |
| 2004/0100384 | A1 | * | 5/2004 | Chen et al. ............... 340/572.1 |
| 2004/0198117 | A1 | * | 10/2004 | Caudell ...................... 442/181 |
| 2005/0000135 | A1 | * | 1/2005 | Trigger ........................ 40/664 |

* cited by examiner

*Primary Examiner*—Katherine Moran
(74) *Attorney, Agent, or Firm*—Michael B. Fein; Cozen O'Connor, P.C.

(57) ABSTRACT

An improved goggle strap is provided. The strap allows for comfortable use through the employment materials such as high density polyester materials that can encase elastic materials. These straps may also contain traceability elements that allow for the easy association of the strap and goggles with user.

9 Claims, 4 Drawing Sheets

GOGGLE STRAP

FIELD OF THE INVENTION

The present invention relates to the field of straps for use in connection with goggles and other protective eyewear.

BACKGROUND OF THE INVENTION

Protective eyewear is an important component of ensuring the safety of personnel who are involved in manufacturing, processing, research and development, and medicine. It is also used in recreational activities such as squash and snorkeling.

Protective eyewear minimizes the risk that an undesirable or noxious substance will come into contact with an individual's eyes. Typically, protective eyewear exists in the form of goggles, and in some instances protective eyewear may be referred to as "safety goggles."

One obvious limitation of protective eyewear is that it is only effective if it stays on a wearer's face. In order to keep goggles or other protective eyewear on one's face, straps may be used. Typically, a strap rests along the rear side of a wearer's head, and through the use of tension, facilitates keeping the goggles in place over the wearer's eyes.

Unfortunately, current goggle straps suffer from at least three problems. First, within a given laboratory, industrial site, sports facility or other location, many sets of goggles and straps look alike, and thus are difficult to clean on a large scale while retaining the identity of the previous wearer. Second, currently available strap materials are prone to particulation; they can shred, hold particulates, shed, etc. Third, current straps are often difficult to adjust for a person's head size while retaining the wearer's comfort; this is particular problematic for neoprene straps. The present invention addresses these issues by providing improved goggle straps.

SUMMARY OF THE INVENTION

The present invention is directed to improved goggle straps that may for example, be used in manufacturing, processing and research facilities. The goggle straps of the present invention may possess one or more of the following benefits: improved comfort; improved durability, and/or improved traceability.

According to a first embodiment, the present invention is directed to a goggle strap comprised of: (a) a first material, wherein said first material is elastic; (b) a second material, wherein said second material encases at least substantially all of said first material, and said second material is longer than said first material; and (c) a traceability element. The second material may be a cleanroom fabric, e.g., polyester, or other fabrics such as a flame retardant material (e.g., Nomex ®heat resistant material made of fire-retarding aramide fibers) or polyester taffeta weaves.

According to a second embodiment, the present invention is directed to a goggle strap comprised of: (a) a first material, wherein said first material is elastic; and (b) a second material, wherein said second material encases at least substantially all of said first material, and said second material is longer than said first material.

According to a third embodiment, the present invention is directed to a goggle strap comprised of: (a) a first material, wherein said first material is elastic and said first material is shorter than the length of the goggle strap; and (b) a traceability element.

According to a fourth embodiment, the present invention is directed to a goggle strap comprised of: (a) a cleanroom fabric; and (b) a traceability element.

DETAILED DESCRIPTION OF THE INVENTION

Figure 1:
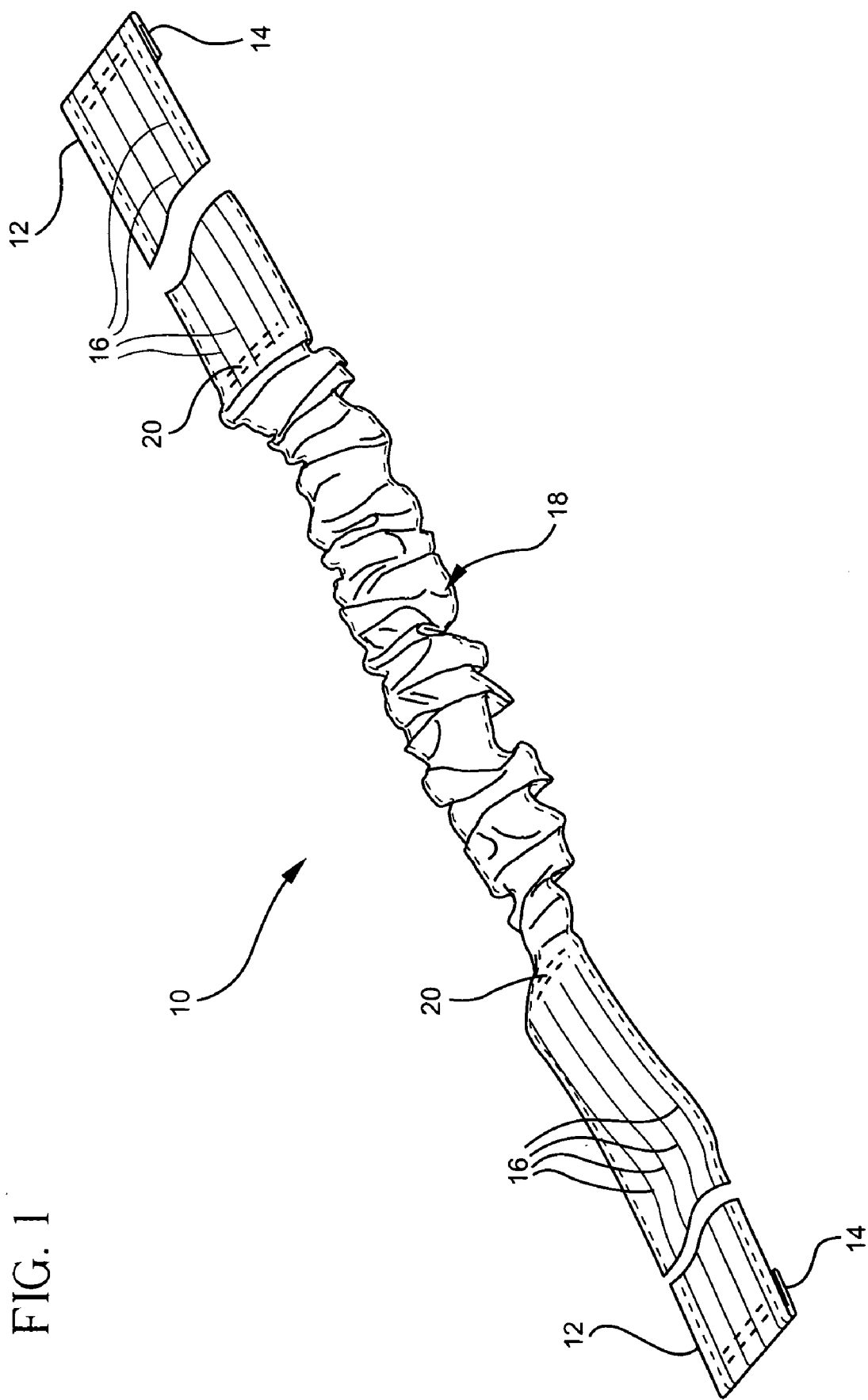
FIG. 1 is a representation of a goggle strap of the present invention in its unextended state.

The present invention will now be described in connection with preferred embodiments. These embodiments are presented to aid in an understanding of the present invention and are not intended, and should not be construed, to limit the invention in any way. All alternatives, modifications and equivalents that may become apparent to those of ordinary skill upon reading this disclosure are included within the spirit and scope of the present invention. Further, the present disclosure is not intended to be a treatise on protective eyewear, goggles, polyester fabrics, elastic or carbon filaments, and basic concepts known to those skilled in the art have not been set forth in detail.

According to a first embodiment, the present invention is directed to a goggle strap comprised of: (a) a first material, wherein said first material is elastic; (b) a second material, wherein said second material encases at least substantially all of said first material, and said second material is longer than said first material; and (c) a traceability element.

The elastic of the first material may be any type of material that can expand and contract to approximately its size before expansion. Thus, unless otherwise specified, the term "elastic" refers to the behavior of the material and not to its composition. Preferably, the elastic is substantially longer than it is wide. For example, it may be rectangular or elliptical. Further, preferably the elastic has the potential to expand a greater distance along its longer axis than along its shorter axis. In some embodiments, the elastic will be between 4 and 12 inches long when expanded and between 2 and 8 inches prior to expansion. More preferably, the elastic will be between 6 and 10 inches when expanded and between 4 and 6 inches prior to expansion. Further, in some embodiments, the elastic will preferably be between ½ and 4 inches wide when expanded and between ¼ and 2 inches prior to expansion. More preferably, the elastic will be between ½ and 2 inches wide when expanded and between ¼ and 1 inch prior to expansion.

Examples of elastic materials include but are not limited to yarns such as polyester, polyether, polyolefin, and polyurethane yarns, as well as other materials such as Lycra, Spandex, DowXLA, and materials in the family of rubber based elastics such as neoprene, isoprene, and latex. These types materials are available from commercial vendors, including but not limited to DuPont, Dow, BF Goodrich and other worldwide manufacturers and distributors of materials exhibiting elastomeric properties. Alternatively, the elastic material could be manufactured by any method that is now known or that comes to be known and that one skilled in the art would appreciate as advantageous for use in connection with the present invention.

By way of example, the elastic of a goggle strap may be constructed according to the following specifications: (i) color: any; (ii) width: ⅜"; (iii) width tolerance: +/−1/16"; (iv) yarn %: 75%+/−4; (v) yarn type: polyester; (vi) rubber: 25%; (vii) rubber size: 1,800 YIELD—YDS/LB NOMINAL; (viii) elongation: 125%; and (ix) number of carriers: 25.

The second material may be comprised of a cleanroom fabric. As used herein, a "cleanroom fabric" refers to a synthetic (e.g. polyester) woven fabric that forms a tight barrier resistance to the passage of fluids, particles and bacteria through the fabric. Examples of cleanroom fabrics include polyesters such as polyesters that comprise or are associated with high-density electrostatic dissipative materials. Other materials that may be of use as the second material include, but are not limited to flame retardant materials such as Nomex®, which is the brand name of a flame retardant meta-aramid material marketed and first discovered by DuPont in the 1970s, and taffeta. Flame retardant materials such as Nomex® can be created by weaving an inherently flame retardant non-oxidizing thread into a polyester material such as Chemstat #919® conductive grid-containing fiber.

When the second material is polyester for use in a cleanroom, preferably, the polyester comprises or is associated with an electrostatic dissipative material. Any type of polyester material that is sufficiently durable and flexible to withstand being put on and off of a person's head may be used in connection with the present application. However, preferably, the polyester has one or more, if not all of the characteristics provided below.

Thus, for cleanroom application, the composition of the second material is preferably at least 90% high-density polyester, more preferably between 95% and 99.5% high-density polyester and most preferably between 98.5% and 99.5% high-density polyester. The high-density polyester comprises or may be associated with an electrostatic material. When the second material comprises polyester, preferably the second material contains up to 10% carbon in the form of a carbon filament, more preferably between 0.25% and 5% carbon, and most preferably between 0.5% and 1.5% carbon. In one preferred embodiment the second material is a fabric that is comprised of approximately 99% high-density polyester and approximately 1% carbon. These percentages are understood by persons skilled in the art to have a variability range of plus or minus 0.25% unless otherwise specified.

When the second material is polyester, preferably it weighs between 1.5 and 4.0 ounces per yard, more preferably between 2.0 and 3.5 ounces per yard and most preferably between 2.5 and 3.0 ounces per yard. The weight measurements may be made pursuant to the ASTM D-3886 test method, which is well known to persons of ordinary skill in the art.

Further, when the second material is polyester, preferably it is constructed at 150-170 ends per inch and 85-100 picks per inch. The construction measurements may be made pursuant to the ASTM D-3775 test method, which is well known to persons of ordinary skill in the art.

The weave of the polyester is preferably a plain weave, which is a type of weave that is well-known to persons of ordinary skill in the art. The advantage of a plain weave is that it is relatively inexpensive to produce when compared to other weaves. However, other weaves can be used in connection with the present invention.

The tensile warp of any cleanroom fabric that is used is preferably at least 150 pounds, more preferably at least 200 pounds, and most preferably at least 210 pounds. The tensile fill is preferably at least 82 pounds, more preferably at least 100 pounds, and most preferably at least 120 pounds. These parameters may be measured according to the ASTM 5034 test method, which is well known to persons of ordinary skill in the art.

The moisture vapor transmission of any cleanroom fabric that is used is preferably between 1100 and 1700 grams/m$^2$/24 hour period, more preferably between 1200 and 1400 grams/m$^2$/24 hour period and most preferably between 1175 and 1272 grams/m$^2$/24 hour period. The moisture vapor transmission may be measured according to the ASTM E-96 test method, which is well known to persons of ordinary skill in the art.

The suter hydrostatic speed (the amount of pressure required to force water through fabric—measured in 'pressure') of any cleanroom fabric that is used is preferably between 500 and 900, more preferably between 600 and 800 and most preferably between 650 and 750. The suter hydrostatic speed may be measured according to the AATCC 127 test method, which is well known to persons of ordinary skill in the art.

The static decay time of any cleanroom fabric that is used is preferably less than 20 seconds, more preferably less than 2 seconds and most preferably less than 0.01 seconds. The static decay time refers to the time that it takes for a charge to dissipate to 10% of its original charge (or 500 volts) and may be measured according to the ESD STMJ 2.1 test method, which is well known to persons of ordinary skill in the art.

The surface resistivity of the cleanroom fabrics is preferably less than $1\times10^{11}$ ohms and more preferably less than $1\times10^{8}$ ohms. The surface resistivity may be measured according to the ESD STMJ 2.1 test method, which is well known to persons of ordinary skill in the art.

Preferably, the second material is between 25 and 33 inches in length and 1 and 2.75 inches wide. Although the second material may fold on itself or bunch up when the elastic is not extended, the length and width of the second material itself essentially do not change, and their measurements are most easily taken when the material is not bunched up. More preferably, the second material is between 27 and 31 inches long and 1.5 and 2.5 inches wide. Most preferably, the second material is between 29 and 30 inches long and 1.75 and 2.25 inches wide.

A small portion of each end of the second material may be folded on itself and they are attached. When the ends of the second material are folded on themselves, the stitched or otherwise affixed in order to prevent unthreading of the goggles to which folded-over portions are not included twice in the aforementioned reference to the length of the second material. Thus, the measurements described above refer to a strap for which any folding over has already occurred.

Examples of second materials that comprise polyester only or polyester containing high-density electrostatic dissipative materials that are commercially available include, but are not limited to, the following brands: Burlington HD ESD C3®, Maxima® ESD, Conductor, Integrity (e.g., Integrity 1600®, 1700®, 2000®), Stern and Stern's Chemstat (e.g., CHEMSTAT 909 Series®, CHEMSTAT 919 Series®, CHEMSTAT 949 Series®), WKEP 3000 (manufacturing by White Knight), Blank Textile cleanroom products and Starshield cleanroom products.

As noted above, the second material may have electrostatic dissipation properties because it comprises or is associated with a carbon filament or another substance in combination with or instead of the carbon filament that provides a similar function, such as stainless steel. Thus, use of carbon filaments, stainless steel and other similar materials in connection with polyester materials serves the function of electrostatic dissipation. For example, polyester materials that comprise or are associated with carbon filaments have been used in applications that include, but are not limited to garments used in the aerospace, microelectronic, nuclear, pharmaceutical, and biotechnology industries.

The carbon filament preferably runs at least 50% more preferably at least 80% of the entire length of the second material. More preferably, the carbon filament runs the entire length of the second material. The carbon filament should be sufficiently electrostatically dissipative while being flexible enough to be used with the second material. Thus, exemplary carbon filaments, include those of the size 25-60 denier, more preferably, 30-55 denier and most preferably 35-45 denier, e.g., approximately 40 denier. Carbon filaments may be purchased from companies such as Teijin in Japan.

When a carbon filament is present, preferably the filament is present in a sufficient amount to provide for adequate dissipation of electrostatic materials. For example, in some applications it may be advantageous to have 2, 3, 4, 5, 6, or 7 carbon filaments that run substantially the whole length, and more preferably the whole length of the second material. One factor that impacts on the upper limitation on the amount of carbon filament is cost. However, in some industries such as the microelectronics industry, the benefit of significant amounts of carbon filament (e.g., greater than an equivalent of 7 filaments of 40 denier) may be worth the cost. A person of ordinarily skill in the art would appreciate that the amount of carbon can be varied by the number and size of the filaments.

The carbon filament may be incorporated into the weave of the second material by any method that is now known or that comes to be known and that a person of ordinary skill in the art would appreciate as being useful in connection with present invention e.g. further weaving or stitching.

When the second material is taffeta, preferably no carbon filament or electrostatic dissipative material is used. When the second material is flame retardant, it may, depending of the environment in which the material will be used, be advantageous to use a carbon filament. For example, Chemstat #487 and Chemstat #919 incorporate carbon filaments.

Preferably, the second material encases at least substantially all of the first material. The phrase "at least substantially all" as used in this document means at least 50%. More preferably 80% of the first material is encased, and most preferably 100% of the first material is encased. The term "encased" refers to the portion of the first material that is not in contact with the wearer or ambient air because it is covered by the second material. Thus, unless otherwise indicated, the percentage is cumulative of the entire surface area of the first material. The term "covered" does not require visual obstruction. Accordingly, part or all of the second material may be translucent or transparent.

In order to secure the first material within the second material, preferably an encasing thread or yarn is used. The encasing thread or yarn may be any material that effectively maintains the first material within a desired area of the second material, e.g., polyester.

The encasing thread or yarn may be used to stitch the ends of the first material to the second material, preferably at locations not at the termini of the second material. Preferably, the first material is located in the approximate center of the second material and the encasing thread or yarns and is affixed, by for example stitching the first material to the second material at the two longitudinal ends of the first material. The same type of encasing thread (e.g., a polyester thread or yarn) may be used to affix the two sides of the second material to each other, thereby enclosing the first material.

The traceability element of the present invention permits a strap and the accompanying pair of goggles to be associated with a unique person. A "traceability element" is a tag or label that may, unless otherwise specified, be any identifier that is different from all other identifiers within a given set, such as a barcode. The traceability element is preferably affixed to the second material by, for example, stitching. Further it is preferably located on a side of the finished strap that is not in contact with the user's head. This side may be referred to as the exterior side of the strap. Similarly, the side to be in contact with a wearer's head is the interior side of the strap.

The goggle strap may be used in connection with any type of eyewear (e.g., goggles or glasses), and preferably is used with protective eyewear such as safety goggles. The strap may be manually affixed to the goggle through attachment points on the protective eyewear, e.g., an orifice that allows for threading.

According to a second embodiment, the present invention is directed to: (a) a first material, wherein said first material is elastic; and (b) a second material, wherein said second material comprises a cleanroom fabric, such as polyester, or a fire retardant material or taffeta, said second material encases at least substantially all of said first material, and said second material is longer than said first material. This embodiment differs from the first embodiment in that there need not be a traceability element. The other parameters for the first and the second material are preferably the same as for the first embodiment.

According to a third embodiment, the present invention is directed to a goggle strap comprised of: (a) first material, wherein said first material is elastic and said first material is shorter than the length of the strap; and (b) a traceability element, wherein said traceability element preferably comprises a barcode. The parameters for the first material and the traceability element of this embodiment are the same as for the first embodiment. However, unlike the first embodiment, there need not be a second material that encases any part of the elastic. Alternatively, less than substantially all of the elastic may be encased in a second material.

For example, approximately 50%, less than 50%, less than 40%, less than 30%, less than 20%, less than 10%, less than 5%, less than 2% or none of it may be encased. In some embodiments the second material might not be contiguous, thereby forming a first portion and a second portion of the second material. The first portion may be attached to a first end of the elastic and the second portion may be attached to the second end of elastic. Further, if the second material is not contiguous, each portion may be comprised of the same or different materials. According to this embodiment preferably, the length and width of the elastic are within the parameters described above.

Alternatively, the first material, e.g., the elastic may be in two or more parts. Thus, there may be a first and a second elastic portion substantially or completely within one second material. Alternatively, there may be an first outer second material connected to a first elastic material on a first side of said first elastic material, an inner second material connected on its first side to the second side of said first elastic material and on its second side to the first side of a second elastic material. The second elastic material may, on its second side be connected to the second outer second material. Thus, the strap may appear with the following components in the following order: first outer second material, first elastic material, inner second material, second elastic material, second outer second material. According to this embodiment, the elastic materials would not be centered on the rear portion of the wearer's head, and instead may be centered closer to each ear of the wearer. The second material for this embodiment, if present, can be any material that is durable and flexible for use in putting on and off of a wearer's head. The first outer second material, inner second material, and the second outer second material may be contiguous, thereby encasing part or all of the first and second elastic materials. Alternatively, they could be separate and distinct, i.e., not contiguous.

When the elastic is in two separate pieces, e.g., first elastic material and second elastic material, the two pieces when combined should stretch to between 8 and 12 inches. Thus, for example, each piece may be 2-4.5 inches long (preferably 3-4 inches long) when unextended with the capability of stretching to 4-6 inches each. Regardless of the number of elastic pieces and pieces of second materials, it is always possible to add a traceability element, e.g. a barcode.

According to a fourth embodiment, the present invention is directed to a goggle strap comprised of: (a) a polyester material; and (b) a traceability element. This embodiment differs from the first embodiment in that there is no requirement of elastic. However, as with first embodiment, preferably, the polyester material is associated with or is itself a high-density electrostatic dissipative material. Further, preferably, the goggle strap comprises a carbon filament. Additionally, preferably, the traceability element is computer readable and more preferably comprises a barcode.

All of the embodiments of the present invention may be used with protective eyewear. The phrase "protective eyewear" refers to any material such as glasses or goggles that may protect the eyes from contact with undesirable or noxious substances. The protective eyewear will preferably be made of plastic, glass or other material that is partially or wholly transparent or translucent. Further, protective eyewear will preferably be protective against materials that might be propelled from in front of, above, below or from the sides of a wearer. It should be noted that although this invention is particularly beneficial for use with protective eyewear, it is of course also useful in connection with eyewear that is used primarily to aid in vision, e.g., eyeglasses to correct near-sightedness, far-sightedness, and/or astigmatisms, as well as sunglass.

The strap of the first embodiment of the present invention may be made by cutting a polyester material of the desired length that is twice as wide as is desired. The polyester material will preferably be purchased with the carbon filament or stainless steel material already present, for example from one of the following fabric manufacturers; Burlington Industries, Blank Textiles, White Knight Engineered Products, and many others. Additional suppliers of this fabric include, but are not limited to HiTec Manufacturing, Vidaro, White Knight Engineered Products. The polyester material may then be folded in half along its longer axis. The elastic may then be tacked in at a location approximately along the center of the length of the polyester material and the elastic then may be sewn to the polyester material at the ends of the elastic material when the elastic is extended. The polyester material may then be sewn along its edges. Finally, the traceability element may be added, by for example sewing it to the polyester material.

The goggle straps of the other embodiments may be made by modifications of the above-described method for making the strap of the first embodiment. For example, the second embodiment may be made in the same manner as the first embodiment, omitting the step of affixing the traceability element. Similarly, the third embodiment may be made in a manner similar to making the first embodiment, but using any type of material, and not necessarily one that encompasses more than 50% of the first material. Finally, the fourth embodiment may be made in a similar manner in which the first embodiment is made, but the elastic can be omitted.

The straps of the present invention may be threaded through orifices on each side of protective eyewear. The orifices may further comprise locks that prevent movement of a strap through them. Examples of these types of locks include any items or materials acceptable for cleanroom use or other method for affixing straps to eyewear.

Various embodiments of the present invention are further illustrated by the figures. In FIG. 1, a goggle strap, 10, is shown is its unextended state. The first material is elastic that has not been extended and is completely encased at 18. The ends of the elastic may be sewn to the second material, 12 at 20. Running the length of the second material are four carbon filaments, 16. Each of the ends of the second material may be sewn to themselves, 14.

Figure 2:
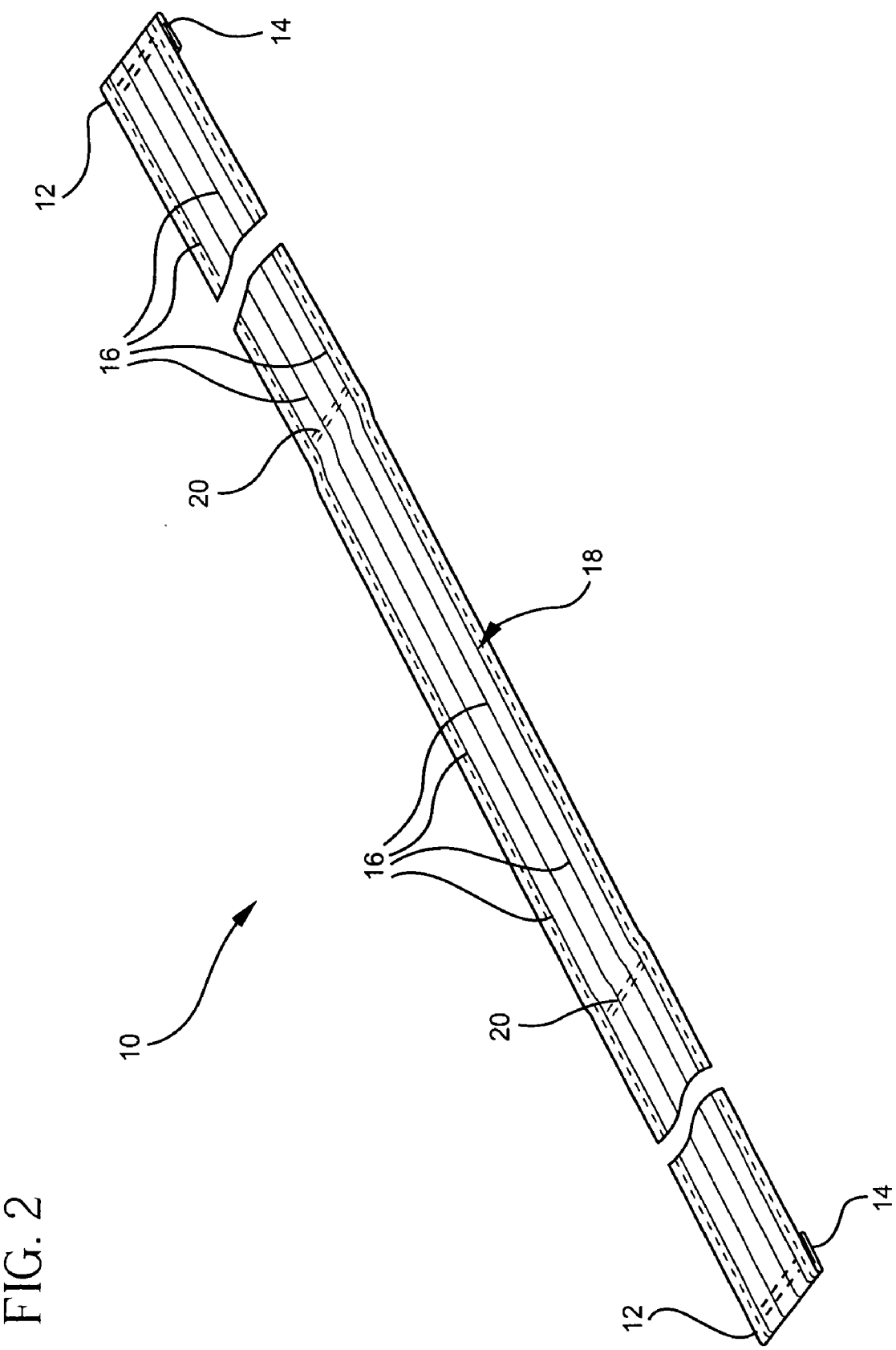
FIG. 2 is a representation of a goggle strap of the present invention in its fully extended state.

FIG. 2 also illustrates a goggle strap; however, unlike in FIG. 1, the strap, 10, is in its extended state. Thus, the carbon filaments, 16, can be seen to run the over the entire second material, 12, including the part that encases the elastic, 18. For reference to comparison to FIG. 1, the location of the affixing of the elastic to the second material, 20, as well as the terminal stitching, 14, of the second material, 12, are shown.

Figure 3:
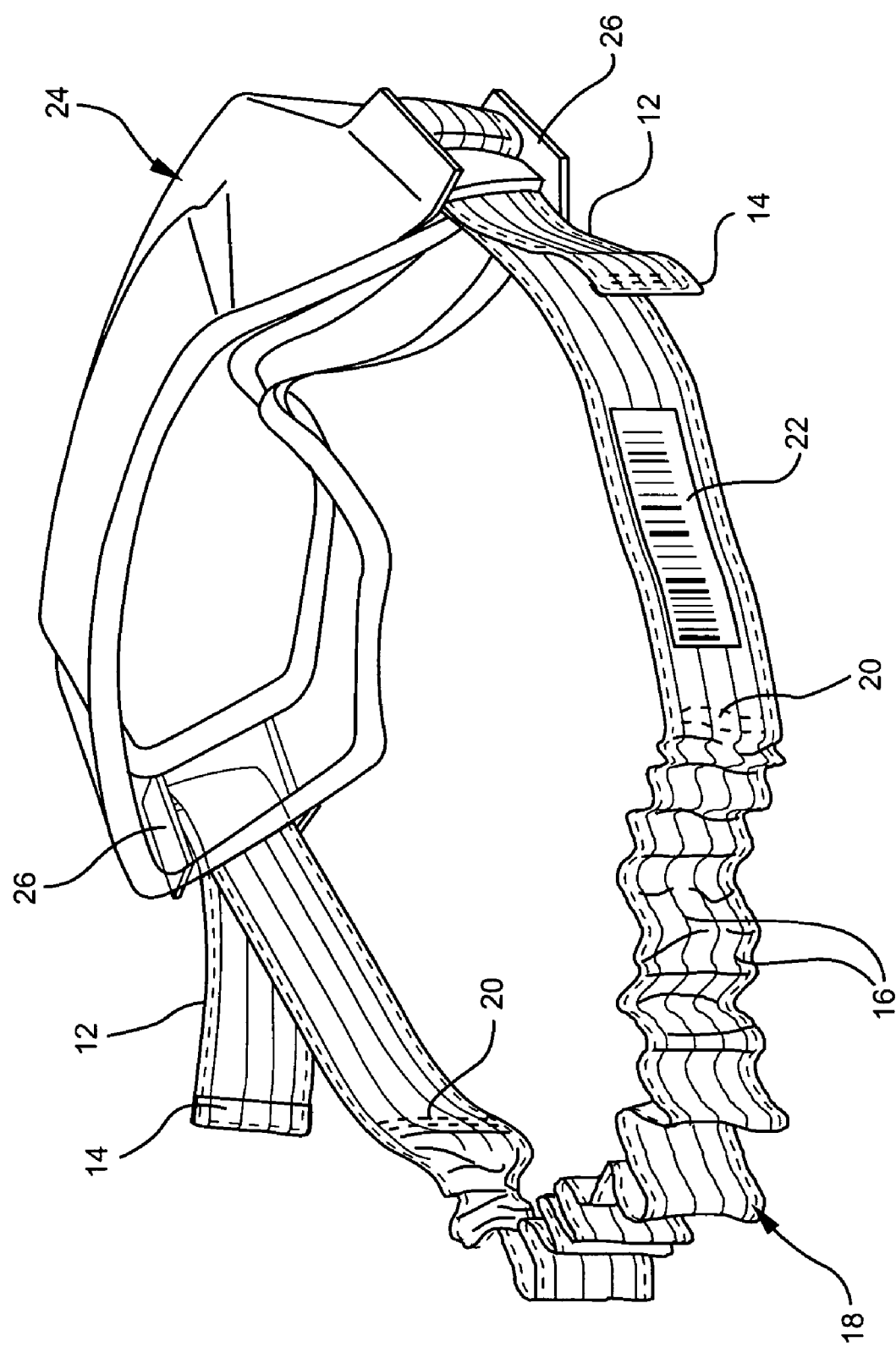
FIG. 3 is a representation of a goggle strap of the present invention in its unextended state that is attached to a pair of goggles.

FIG. 3 illustrates a strap of the present invention that shows a traceability element in the form of a barcode, 22. This figure also shows the goggle strap attached to goggles, 24, through a strap threading structure, 26. As with the other figures, for reference, location of the encased elastic, 18, the carbon filaments, 16, the terminal stitching, 14 of the second material, 12, and the stitching of the elastic to the second material, 20, are shown.

Figure 4:
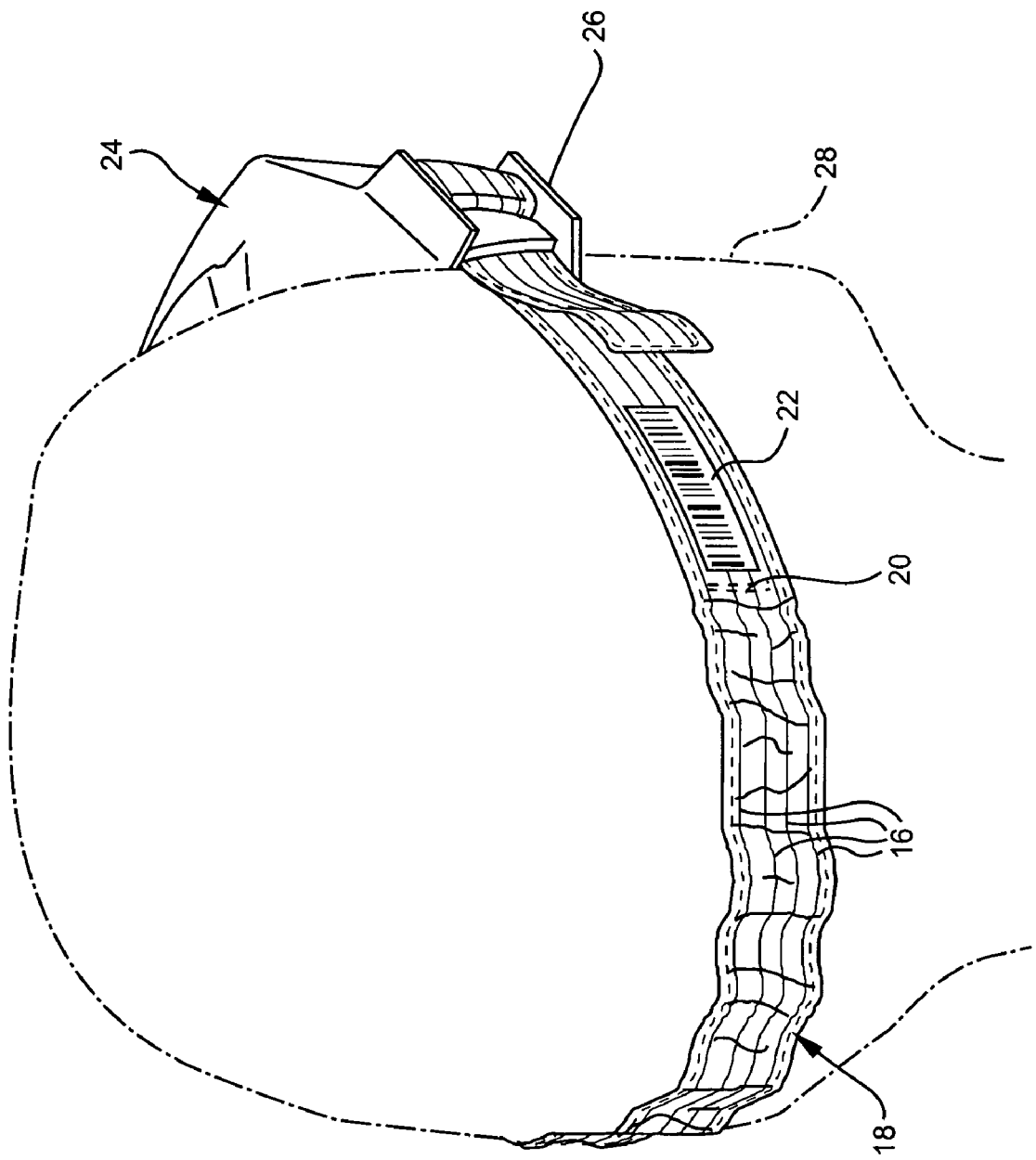
FIG. 4 is a representation of a goggle strap of the present invention as worn by an individual.

FIG. 4 illustrates the use of the goggle strap with a pair of goggles, 24, by an individual, 28. The strap is affixed to the goggles at a threading structure, 26. A traceability element, 22, in the form of a barcode is seen facing away from the wearer's head. The hidden elastic, 18, is partially extended relative to its appearance in FIG. 3. The amount of extension will of course depend on the size of the head of the wearer. For reference, the location of the carbon filaments, 16, and the location of the stitching of the elastic, 20 are also shown.

EXAMPLES

The following examples set forth preferred embodiments of the invention. These embodiments are merely illustrative and are not intended and should not be construed to limit the claimed invention in any way.

Example 1

Affixing Strap to Goggles (Prophetic)

The strap may be affixed to the goggle manually by inserting the goggle strap under the innermost orifice and then weaving the second material back through the outermost orifice. If a locking mechanism is used, it may be employed to prevent unintentional unthreading. If the strap has a traceability element, such as a barcode, the barcode may be affixed before or after the strap is threaded. The barcode may be assigned to the customer's account and once the barcode is associated with an individual, sent to production for processing, e.g., associating with other clothing of the customer.

Example 2

Use of Goggles (Prophetic)

The goggle may be supplied to the user in a sealed cleanroom polybag. The user will open the sealed bag and remove goggle. The strap will be extended to fit over the user's head, with the strap being on the back of the head. If the goggle needs to be tightened the user can pull on the then ends of the strap, towards the back of the head, for easy adjustment. If the strap contains a traceability element, preferably the traceability element will face outward as shown in FIG. 4.

One benefit of the use of an ESD (electrostatic dissipative) strap is that it is easily cleaned in a water wash process that reduces the particulates compared to the neoprene strap that is on other goggles. Another benefit is realized particularly when polyester is the material of the second strap; the polyester encased elastic allows for a more comfortable fit.

Example 3

Tracking Goggles (Prophetic)

The goggles straps and the goggles to which they are affixed may be associated with particular users by for example assigning each user a unique barcode. A plurality of users may use their goggles at a facility. After one or more uses, the plurality of goggles may be collected and sent to a cleaning facility that may be on-site or off-site. The goggles and their straps can be inspected for undesirable attributes, such as rips or tears in the straps, which can be repaired (or the goggles can be replaced). All goggles that are not to be discarded can be sent through a cleaning process. Because all goggles have unique identifiers, they can be cleaned simultaneously and then returned to the wearers.

Having thus described and exemplified the invention with a certain degree of particularity, it should be appreciated that the following claims are not to be so limited but are to be afforded a scope commensurate with the wording of each element of the claims and equivalents thereof.

What is claimed:

1. A goggle strap having a first end and a second end comprised of
    a. a cleanroom fabric selected from the group consisting of at least 90% high density polyester, 95-99.5% high-density polyester, 98.5-99.5% high density polyester, and taffeta, and said fabric comprises an electrostatic dissipative material in the form of at least one carbon filament;
    b. a computer readable traceability element unique to each strap, affixed to the strap.

2. The goggle strap of claim 1, wherein said cleanroom fabric encases an elastic material.

3. The goggle strap of claim 1, wherein said computer readable traceability element comprises a barcode.

4. A safety goggle comprised of the goggle strap of claim 1 and protective eyewear or eyeglasses.

5. The safety goggle of claim 4, wherein the goggle strap is between 25 and 33 inches in length when extended.

6. The safety goggle of claim 5, wherein the cleanroom fabric is between 4 and 12 inches when extended.

7. The goggle strap of claim 1 having a length between 25 and 33 inches when extended.

8. The goggle strap of claim 1 wherein the first material is between 6 and 10 inches when extended.

9. The goggle strap of claim 1 wherein the traceability element is sewn outside or inside the cleanroom fabric.

* * * * *